United States Patent [19]

Brown et al.

[11] 4,013,771

[45] Mar. 22, 1977

[54] SUBSTITUTED 2-AMINOTHIOCHROMONES

[75] Inventors: Richard E. Brown, East Hanover; David M. Lustgarten, Dover, both of N.J.

[73] Assignee: Warner-Lambert Company, Morris Plains, N.J.

[22] Filed: Dec. 15, 1975

[21] Appl. No.: 640,667

[52] U.S. Cl. .......................... 424/275; 260/327 TH
[51] Int. Cl.² ...................................... C07D 335/06
[58] Field of Search ............. 260/327 TH; 424/275

[56] References Cited

UNITED STATES PATENTS

| | | | |
|---|---|---|---|
| 3,804,857 | 4/1974 | Cairns et al. | 260/327 TH |
| 3,825,574 | 7/1974 | Brown | 260/345.2 |
| 3,828,073 | 8/1974 | Zinnes et al. | 260/327 TH |
| 3,853,921 | 12/1974 | Klutchko et al. | 260/345.2 |
| 3,862,140 | 1/1975 | Zinnes et al. | 260/327 TH |
| 3,862,143 | 1/1975 | Klutchko et al. | 260/345.2 |
| 3,868,379 | 2/1975 | Zinnes et al. | 260/294.8 C |
| 3,932,466 | 1/1976 | Brown et al. | 260/345.2 |

*Primary Examiner*—Cecilia Jaisle
*Attorney, Agent, or Firm*—Albert H. Graddis; Frank S. Chow; Anne M. Kelly

[57] ABSTRACT

This invention relates to substituted 2-aminothiochromones of the general structure I:

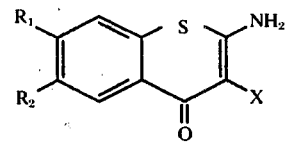

wherein $R_1$ and $R_2$ may be hydrogen; lower alkyl or lower alkoxy of 1 to 6 carbon atoms; or halogen such as chloro or bromo; and X may be cyano or carboxamido. The compounds are prepared using a thiosalicylic acid or a substituted thiosalicylic acid as starting material.

The compounds of this invention are active in the prevention of allergic and asthmatic reactions in mammals.

8 Claims, No Drawings

SUBSTITUTED 2-AMINOTHIOCHROMONES

DESCRIPTION OF THE PRIOR ART

Benzothiopyran derivatives are known. For example, 4-hydroxy-2H-1-benzothiopyran-3-carboxylates are described by T. Moriwake, J. Med. Chem. 9:163 (1966).

Benzothiopyran-3-carboxanilides and their 5-oxides are disclosed in United States Patent No. 3,828,073. And benzothiopyran-3-carboxanilide 1,1-dioxides are disclosed in United States Patent No. 3,862,140.

Additionally, benzopyran and chromone structures having a cyano group in the 3-position are known in the art.

In U.S. Pat. No. 3,825,574, U.S. Pat. No. 3,853,921 and in U.S. Pat. No. 3,862,143, 3-cyano-2-substituted chromones and the preparation thereof are disclosed. The 2-substituent on the chromone compounds of these last-mentioned patents may be hydrogen, lower alkyl, fluorinated lower alkyl, lower alkoxycarbonyl, carboxy, or lower alkyl carboxylic acid. And in U.S. Ser. No. 532,417, filed Dec. 13, 1974, now 3,932,466, 2-aminochromones having either a 3-cyano or 3-carboxamido substituent are disclosed.

DESCRIPTION OF THE SPECIFIC EMBODIMENTS

This invention relates to novel substituted 2-aminothiochromones of the general structure I:

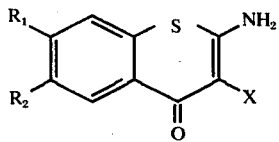

In the above structure $R_1$ and $R_2$ may be hydrogen, lower alkyl or lower alkoxy of 1 to 6 carbon atoms, or halogen such as chloro or bromo; and X may be cyano or carboxamido.

The compounds of this invention are prepared using a thiosalicylic acid or a substituted thiosalicylic acid of structure II as the starting material. In structure II, $R_1$ and $R_2$ are as defined for structure I.

In the first step, the mercapto group of the starting thiosalicylic acid is protected by conversion to an acylthio group, such as a thioacetyl group, to give a compound having structure III. In structure III, $R_1$ and $R_2$ are as defined for structure I, and $R_3$ may be lower alkyl of 1 to 5 carbon atoms. Among the reagents which may be used for the conversion in step one are acid chlorides, such as acetyl chloride or acid anhydrides, such as acetic anhydride.

In the second step, the acylthio derivative having structure III is converted to its acid chloride of structure IV in which $R_1$ and $R_2$ are as defined for structure I. Among the reagents which may be used for this reaction are thionyl chloride, oxalyl chloride or, preferably, phosphorous pentachloride.

In the third step, the acid chloride having structure IV is reacted with malononitrile in the presence of a basic catalyst and solvent to give the compound according to structure I wherein X is cyano. Among the basic catalysts which may be used there may be mentioned triethylamine, alkali metal hydrides such as sodium hydride, alkali metal hydroxides, amides of the formula $M-NH_2$ wherein M is an alkali metal (potassium amide and the like), and alkoxides of the formula R-O-M wherein R is a lower alkyl group of 1 to 6 carbon atoms and M is an alkali metal. Among the suitable solvents which may be used are water, benzene, toluene, tetrahydrofuran, and dimethylformamide. Naturally, the basic catalyst and solvent selected must be compatable, i.e., non-reactant with one another. Preferably, a combination of an alkali metal hydroxide, such as sodium hydroxide, in aqueous medium is used.

In order to prepare those compounds according to structure I wherein X is carboxamido, the compound according to structure I wherein X is cyano is subjected to an acid catalyzed hydrolysis step. Among the acids which may be used for this reaction are mineral acids as hydrochloric, phosphoric, or, preferably, sulfuric acid.

In this invention the thiosalicylic acids used as starting materials are all commercially available or are known compounds prepared by standard methods described in the literature.

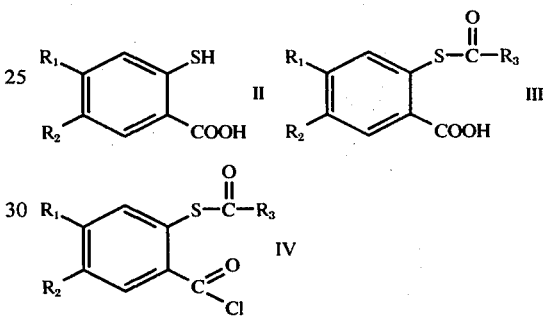

In all of the above Formulas I, II, III and IV, the R group definitions may be more fully described as follows: the term "lower alkyl" is meant to include lower aliphatic hydrocarbons having 1 to 6 carbon atoms in the carbon chain, such as methyl, ethyl, propyl, isopropyl, butyl or isobutyl. This definition for lower alkyl also applies to the lower alkyl portion of "lower alkoxy". The term "lower acyloxy" is meant to include lower alkyl carboxylic acids wherein "lower alkyl" has the aforementioned meaning. The term "halogen" is meant to include bromine, chlorine, iodine and fluorine.

The compounds of this invention are active in the prevention of allergic conditions (typically, asthmatic reactions) in mammals such as rats and guinea pigs as evidenced by positive results in the passive cutaneous anaphylaxis screen (PCA test). The PCA screen is a modification of the procedure described by I. Mota, Life Sciences, Vol. 4, No. 7: 465–474 (1963) and Z. Ovary and O. Bier, Proc. Soc. Exptl. Biol. Med., 81: 584–586 (1952) and provides a measure of the effectiveness of test compounds in inhibiting the release or action of toxic products arising from the combination of reaginic antibodies with specific antigens. These toxic products are causative factors in such disorders as bronchial allergic asthma (extrinsic reagins), exercise asthma, cold asthma, hay fever, perennial allergic rhinitis, food allergies, serum or drug allergies, insect sting allergies, angioneurotic edema, atopic dermatitis, including infantile eczema, urticaria, dermographism, dermatoconjunctivitis, acute allergic conjunctivitis, chronic allergic conjunctivitis, and the like.

Inhibition of reaginic antigen/antibody reactions in experimental animals such as rats and guinea pigs is regarded as representative of inhibition of human reaginic antigen/antibody reactions which occur during allergic episodes.

In the PCA screen, rats are sensitized with 1 mg of ovalbumin (Pentex, Kankakee, Ill.) intramuscularly and with $10^{10}$ B. pertussis organisms (Parke-Davis and Co., Detroit, Michigan; Bio. 210) intraperitioneally. On the 14th day the animals are bled and the serum prepared in the usual manner. The reaginic nature of antiovalbumin serum thus obtained is verified by the use of standard criteria.

Passive cutaneous anaphylaxis is induced as described by Ovary and Bier (1952) and by Mota (1963). Suitable antibody concentration in 0.1 ml to result in reactions between 7 and 19 mm in diameter (usually 1:5 to 1:40 dilutions) are injected intradermally on either side of the dorsal midline of rats. Forty-eight hours later, the animals are dosed with drug and injected in the tail vein with 1 ml of saline containing 0.25% Evans blue and 1 mg ovalbumin. Thirty minutes later animals are sacrificed with ether, the dorsal skin reflected, and the mean orthogonal diameter of the reaction site measured.

A linear relationship can be shown to exist between the relative antibody concentration and the diameter of the resultant reaction if the antibody concentration is adjusted to yield diameters between approximately 7 and 19 mm. For each experiment, a line is fitted by the least squares method for the relationship of the diameter to the relative antibody concentration. This line is extrapolated to zero antibody concentration to derive the base-line diameter. The percentage inhibition due to drug treatment is then calculated by the formula:

$$\% \text{ inhibition} = \left[ 1 - \frac{\text{(diameter of experimental-base value)}}{\text{(diameter of control-base value)}} \right] \times 100$$

The significance of the inhibition is measured by Student's t-test.

For administration, the compounds are suspended by trituration in 1% gum tragacanth and 0.15M saline so as to give 10 ml/kg body weight.

Thus, the compounds of this invention are active for the inhibition of reagin-mediated allergic disorders when administered to mammals in need thereof at dose levels of from about 5 to about 100 mg/kg of body weight, by the oral or parenteral route. This dosage may be varied depending upon the severity of the condition, the age, weight, sex and class of mammal being treated, as well as the route of administration.

In use, the compounds of the invention may be combined with parenterally acceptable vehicles, such as gum tragacanth, in saline suspension, to provide dosage forms suitable for parenteral administration; or they may be combined with pharmaceutical diluents such as lactose, cornstarch, and the like and formulated into tablet or capsule dosage forms.

To further illustrate the practice of this invention, the following examples are included:

EXAMPLE 1

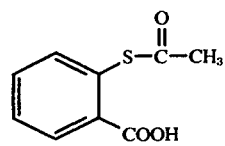

To an ice cold solution of 5.6g of potassium hydroxide in 56ml of water is dissolved 6.16g of thiosalicylic acid. To this is added 50g of ice and 5.0g of acetic anhydride, and the mixture is stirred for 1 hour. The mixture is acidified with 4N HCl. The solid is filtered and taken up in benzene. The benzene layer is washed with water, dried with magnesium sulfate containing decolorizing carbon, then concentrated to 100ml volume. On dilution with 300ml of hexane, 5.5g of crystals separated, mp. 125°–6° C. [reported 125° C.(O. Hinsberg, Chem. Ber., 43: 654 (1910))].

EXAMPLE 2

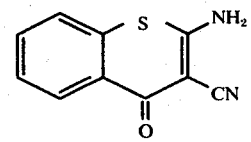

2-Amino-4-oxo-4H-1-benzothiopyran-3-carbonitrile.

To a suspension of 19.2g of thioaspirin in 100ml of benzene is added slowly 25.4g of oxalyl chloride. The clear solution is refluxed for 15 min. and then concentrated under partial vacuum to a thick oil. This is added all at once with stirring to an ice-cold suspension of 14g of malononitrile in 200ml of 1% sodium hydroxide solution. After 5 min. stirring, a second portion of malononitrile and 10ml of 20% sodium hydroxide is added. The mixture is stirred for 20 min., warmed to 40° and 50% potassium hydroxide added slowly until a complete solution is obtained. The mixture is cooled and acidified with conc. HCl. The solid is filtered, washed with water and recrystallized from methanol for analysis, mp. 295°–9° C.

Anal. Calcd. for $C_{10}H_6N_2OS$: C, 59.39; H, 2.99; N, 13.85. Found: C, 59.20; H, 3.18; N, 13.67.

EXAMPLE 3

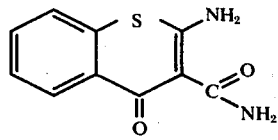

2-Amino-4-oxo-4H-1-benzothiopyran-3-carboxamide.

A mixture of 3.75g of 2-amino-4-oxo-4H-1-benzothiopyran-3-carbonitrile, 4ml of water and 16ml of conc. sulfuric acid is stirred and heated on a steam bath for 3 hours. The mixture is poured into ice water and the solid filtered and recrystallized from methanol, mp. 277°–9° C.

Anal. Calcd. for $C_{10}H_8N_2O_2S$: C, 54.53; H, 3.66; N, 12.72. Found: C, 54.42; H, 3.75; N, 12.58.

We claim:

1. A compound of the Formula I:

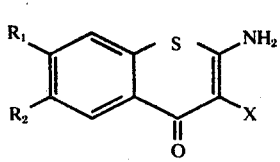

wherein $R_1$ and $R_2$ each represent hydrogen, lower alkyl of 1 to 6 carbon atoms, lower alkoxy of 1 to 6 carbon atoms or halogen; and X represents cyano carboxamido.

2. A compound according to claim 1 which is 2-amino-4-oxo-4H-1-benzothiopyran-3-carbonitrile.

3. A compound according to claim 1 which is 2-amino-4-oxo-4H-1-benzothiopyran-3-carboxamide.

4. A process for the production of a compound of the Formula I:

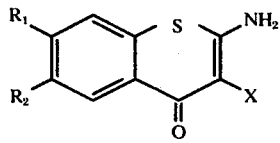

wherein $R_1$ and $R_2$ each represent hydrogen, lower alkyl of 1 to 6 carbon atoms, lower alkoxy of 1 to 6 carbon atoms or halogen; and X represents cyano or carboxamido, which comprises:

A. Treating a compound of the Formula II:

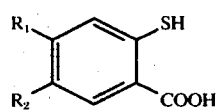

wherein $R_1$ and $R_2$ are as defined above in Formula I with an acid chloride or an acid anhydride to convert the free mercapto group to an acylthio group and obtain a compound of the Formula III:

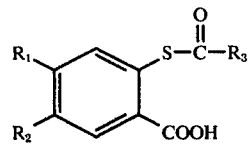

wherein $R_1$ and $R_2$ are as defined above in formula I, and $R_3$ represents 1 to 5 carbon lower alkyl;

B. Treating Compound III with a reagent selected from the group consisting of thionyl chloride, oxalyl chloride, and phosphorous pentachloride to obtain a compound of the Formula IV:

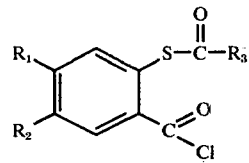

wherein $R_1$, $R_2$ and $R_3$ are as defined above in Formula I;

C. Treating a solution of Compound IV with malononitrile in the presence of a basic catalyst to obtain Compound I wherein X is cyano, which is subjected to acid catalysed hydrolysis to obtain Compound I wherein X is carboxamido.

5. A process according to claim 4 wherein, in Step A, an acid derivative selected from the group consisting of acetyl chloride and acetic anhydride is used.

6. A process according to claim 4 wherein, in Step C, the solvent is selected from the group consisting of water, benzene, toluene, tetrahydrofuran and dimethylformamide.

7. A process according to claim 4 wherein, in Step C, the basic catalyst is selected from the group consisting of triethylamine, alkali metal hydrides, alkali metal hydroxides, amides of the formula M-NH$_2$ wherein M is an alkali metal, and alkoxides of the formula R-O-M wherein R is a 1 to 6 carbon lower alkyl group and M in an alkali metal.

8. A method for preventing allergic manifestations in a mammal in need thereof which comprises administering an effective amount of a compound of the Formula I:

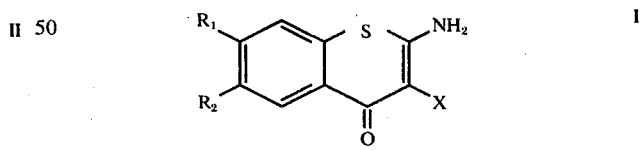

wherein $R_1$ and $R_2$ each represent hydrogen, lower alkyl of 1 to 6 carbon atoms, lower alkoxy of 1 to 6 carbon atoms or halogen; and X represents cyano or carboxamido.

* * * * *